United States Patent
Favero et al.

(10) Patent No.: US 10,662,149 B2
(45) Date of Patent: May 26, 2020

(54) METHOD FOR PRODUCING THE 2-ACRYLAMIDO-2-METHYLPROPANE SULFONIC ACID MONOMER AND POLYMER COMPRISING SAID MONOMER

(71) Applicant: S.P.C.M. SA, Andrezieux Boutheon (FR)

(72) Inventors: Cédrick Favero, Saint Romain le Puy (FR); Johann Kieffer, Hopital le Grand (FR)

(73) Assignee: S.P.C.M. SA, Andrezieux Boutheon (FR)

( * ) Notice: Subject to any disclaimer, the term of this patent is extended or adjusted under 35 U.S.C. 154(b) by 98 days.

(21) Appl. No.: 15/753,577

(22) PCT Filed: Sep. 16, 2016

(86) PCT No.: PCT/FR2016/052359
§ 371 (c)(1),
(2) Date: Feb. 20, 2018

(87) PCT Pub. No.: WO2017/046546
PCT Pub. Date: Mar. 23, 2017

(65) Prior Publication Data
US 2018/0244609 A1 Aug. 30, 2018

(30) Foreign Application Priority Data
Sep. 18, 2015 (FR) .................................... 15 58796

(51) Int. Cl.
C07C 303/00 (2006.01)
C07C 303/02 (2006.01)
C07C 303/20 (2006.01)
C07C 303/22 (2006.01)
C08F 20/58 (2006.01)

(52) U.S. Cl.
CPC .......... C07C 303/20 (2013.01); C07C 303/02 (2013.01); C07C 303/22 (2013.01); C08F 20/58 (2013.01)

(58) Field of Classification Search
CPC ... C07C 303/00; C07C 303/02; C07C 303/06; C07C 303/20; C07C 303/22

USPC ........................................................ 562/105
See application file for complete search history.

(56) References Cited

U.S. PATENT DOCUMENTS

| 4,337,215 A | * | 6/1982 | Doi ........................ C07C 309/15 |
| | | | 562/105 |
| 5,185,395 A | * | 2/1993 | Robinson .................. C08F 2/32 |
| | | | 524/457 |
| 6,217,778 B1 | * | 4/2001 | Shing .................... C02F 1/5245 |
| | | | 210/708 |
| 6,313,246 B1 | * | 11/2001 | Carter ....................... C02F 1/56 |
| | | | 526/258 |
| 6,331,647 B1 | * | 12/2001 | Quinn ................... C07C 303/44 |
| | | | 562/105 |
| 6,448,347 B1 | | 9/2002 | Quinn et al. |
| 8,247,601 B2 | | 8/2012 | Wakayama |
| 2013/0137893 A1 | | 5/2013 | Ebel et al. |

FOREIGN PATENT DOCUMENTS

| CN | 101066940 A | * | 11/2007 | ........... C07C 303/06 |
| CN | 102351744 A | * | 2/2012 | ........... C07C 309/15 |
| CN | 102351744 A | | 2/2012 | |
| CN | 104211622 A | * | 12/2014 | ........... C07C 303/02 |
| JP | 3-77860 | * | 4/1991 | ........... C07C 309/15 |
| JP | 5-125037 A | * | 5/1993 | ........... C07C 309/21 |
| JP | 5-163235 A | * | 6/1993 | ........... C07C 309/20 |
| JP | 2010270170 A | | 12/2010 | |
| WO | 2009/072480 A1 | | 6/2009 | |

OTHER PUBLICATIONS

JP 5-125037 (May 21, 1993); machine translation. (Year: 1993).*
International Search Report (and English translation) and Written Opinion of the International Searching Authority for PCT/FR2016/052359 dated Nov. 16, 2016.

* cited by examiner

*Primary Examiner* — Rip A Lee
(74) *Attorney, Agent, or Firm* — Heslin Rothenberg Farley & Mesiti P.C.

(57) ABSTRACT

The invention relates to a method for producing 2-acrylamido-2-methylpropane sulfonic acid. Said method consists in reacting together acrylonitrile, fuming sulfuric acid and isobutylene. It is characterized in that the isobutylene contains less than 1000 ppm of butadiene and less than 1000 ppm of butene.

17 Claims, No Drawings

METHOD FOR PRODUCING THE 2-ACRYLAMIDO-2-METHYLPROPANE SULFONIC ACID MONOMER AND POLYMER COMPRISING SAID MONOMER

CROSS REFERENCE TO RELATED APPLICATIONS

This application is a national stage filing under section 371 of International Application No. PCT/FR2016/052359, filed on Sep. 16, 2016, and published on Mar. 23, 2017 as WO 2017/046546, which claims priority to French Application No. 1558796, filed on Sep. 18, 2015. The entire contents of each of said applications are hereby incorporated herein by reference.

FIELD OF THE INVENTION

The field of the invention relates to a new process for obtaining 2-acrylamido-2-methylpropane sulfonic acid. More specifically, the invention relates to a process for obtaining 2-acrylamido-2-methylpropane sulfonic acid from isobutylene having a butene content less than 1000 ppm and a butadiene content less than 1000 ppm.

PRIOR ART

2-Acrylamido-2-methylpropane sulfonic acid is widely used as an additive in acrylic fibers and as a raw material for obtaining polymers used as dispersant or thickener in various sectors like cosmetics or the oil industry.

The polymers specifically used as thickeners in enhanced oil recovery are produced by the polymerization of several monomers, at least one monomer of which is 2-acrylamido-2-methylpropane sulfonic acid. These polymers generally have very high molecular weights with very low insolubles content in the water.

As an example, document JP2010-270170 describes obtaining high molecular weight polymers containing at least 2-acrylamido-2-methylpropane sulfonic acid and its use in enhanced oil recovery.

2-Acrylamido-2-methylpropane sulfonic acid is commonly made by co-reacting acrylonitrile, fuming sulfuric acid (Oleum) and isobutylene in stoichiometric proportions. However, acrylonitrile is used in excess relative to the fuming sulfuric acid and isobutylene because it acts as reaction solvent.

2-Acrylamido-2-methylpropane sulfonic acid is insoluble in the solvent acrylonitrile, and consequently the reaction product takes the form of crystals suspended in the reaction solvent.

As examples, documents U.S. Pat. No. 6,448,347 and CN 102,351,744 describe a production process for 2-acrylamido-2-methylpropane sulfonic acid in continuous mode.

2-Acrylamido-2-methylpropane sulfonic acid is subsequently separated from the acrylonitrile, generally by filtration, and can later be purified by several known methods. In fact, purification is necessary because a low level of impurities present in 2-acrylamido-2-methylpropane sulfonic acid strongly affects its polymerization, and more specifically the molecular weight and the level of insolubles in the water.

Thus, in document WO 2009/072480, which covers a production process for 2-acrylamido-2-methylpropane sulfonic acid (AMPS), it is explained that 2-methyl-2-propenyl-1-sulfonic acid (IBSA) and 2-methylidene-1,3-propyl-enedisulfonic acid (IBDSA) impurities above a certain concentration strongly affect polymerization.

So, many purification methods exist. As an example, mention may be made of document U.S. Pat. No. 6,331,647, which describes a method for purifying 2-acrylamido-2-methylpropane sulfonic acid by recrystallization from its sodium salt, with water as the recrystallization solvent. However, since 2-acrylamido-2-methylpropane sulfonic acid salts are very water soluble (>150 g/L), the recrystallization process is complex and burdensome, resulting in a low yield.

Document U.S. Pat. No. 4,337,215 describes a 2-acrylamido-2-methylpropane sulfonic acid purification method by recrystallization in acetic acid, by hot dissolution and crystallization by progressive cooling. Despite the good purity of the resulting 2-acrylamido-2-methylpropane sulfonic acid, the process, whose yield is limited, calls for multiple dissolution/cooling steps and requires the acetic acid used to be distilled to regenerate it before later reuse in a new 2-acrylamido-2-methylpropane sulfonic acid recrystallization batch.

Document US 2013/0137893 describes a purification method for 2-acrylamido-2-methylpropane sulfonic acid by recrystallization of its sodium salt in an anhydrous solvent. The process is complex, calling for organic solvents and anhydrous bases that are difficult to handle. What is more, this document does not mention the impurities created by the Michael addition of the anhydrous base on the 2-acrylamido-2-methylpropane sulfonic acid double bond.

2-Acrylamido-2-methylpropane sulfonic acid quality therefore remains a major problem for the production of polymers comprising this monomer. Therefore, a simple process is necessary for the production of high purity 2-acrylamido-2-methylpropane sulfonic acid, without recourse to complex and burdensome purification steps sometimes using products that are difficult to handle.

In the prior art, the impurities and isobutylene quality are never taken into consideration for the production of 2-acrylamido-2-methylpropane sulfonic acid.

DESCRIPTION OF THE INVENTION

The present invention relates to a production process for 2-acrylamido-2-methylpropane sulfonic acid consisting of co-reacting acrylonitrile, fuming sulfuric acid and isobutylene. In this process, the isobutylene contains less than 1000 ppm of butadiene and less than 1000 ppm of butene.

The reaction used in the process for preparation of 2-acrylamido-2-methylpropane sulfonic acid follows the reaction scheme below, in which acrylonitrile is present in excess so as to be both solvent for the reaction and a reagent. Acrylonitrile is put in contact with fuming sulfuric acid and isobutylene. The sulfuric acid used may further comprise variable free $SO_3$ proportions.

According to the invention and in a preferred manner, the sulfuric acid has a concentration of between 105.6% and 122.5%, corresponding to Oleum comprising between 25% and 100% free $SO_3$. More preferably, the sulfuric acid has a concentration of between 105.6% and 113.5%, corresponding to Oleum comprising between 25% and 60% free $SO_3$.

The percentage of free $SO_3$ is determined relative to the percentage of $H_2SO_4$ according to the following formula:

$$\%SO3 = \frac{(\% H2SO4 - 100) * M_{SO3}}{M_{H2O}}$$

According to a specific embodiment, the SO₃ and water can also be added separately. The alpha, beta and gamma forms of SO₃ can be used interchangeably in the present invention.

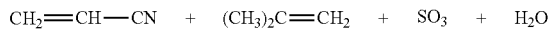

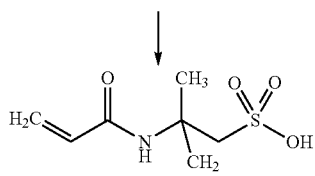

Reaction Scheme for Preparation of 2-Acrylamido-2-Methylpropane Sulfonic Acid

The process may be a continuous operation, where the acrylonitrile is first poured, then mixed with sulfuric acid with the temperature being controlled within a range of between −50° C. and 20° C., preferably between −20° C. and 0° C. In a second step, isobutylene is added to the previous mixture (acrylonitrile+fuming sulfuric acid), the temperature being controlled between −40 and 80° C., preferably between 30 and 50° C.

The contact time for isobutylene and previous mixture is advantageously of between 10 seconds and 240 minutes, preferably between 10 minute and 120 minutes.

The molar ratios of reagents are typically determined to maximize the production of 2-acrylamido-2-methylpropane sulfonic acid. The ratio of SO₃ to isobutylene is generally included between 0.2:1 and 2:1, preferably between 0.4:1 and 1.5:1, and more preferably between 0.7:1 and 1.2:1.

The ratio of acrylonitrile to isobutylene is included between 1:1 and 20:1, preferably between 6:1 and 18:1, and more preferably between 12:1 and 16:1.

When the isobutylene is added, 2-acrylamido-2-methylpropane sulfonic acid crystals precipitate in the medium because they are not soluble in the solvent acrylonitrile, and consequently the reaction product takes the form of crystals suspended in the reaction solvent.

Isobutylene can be added to the mixture in gaseous form, pure or diluted with a neutral gas, or else in liquefied gas form, or dissolved in a solvent. The reaction from addition of isobutylene can be done under atmospheric pressure or else under higher pressure, for example up to 1.2 MPa (12 bars) relative.

The crystals of 2-acrylamido-2-methylpropane sulfonic acid are then separated from the solvent by a liquid/solid separation step. As examples and in a non-limiting manner, we can cite the use of a centrifugal filter, a decanter, a filter press, a belt filter, a disk filter, or a rotating drum filter.

The 2-acrylamido-2-methylpropane sulfonic acid crystals are then advantageously dried under low or atmospheric pressure.

It is also possible to conduct the process as a batch process. Indeed, the 2-acrylamido-2-methylpropane sulfonic acid production process (continuous or batch) does not affect the benefits resulting from the present invention at all. In other words, the present invention is used equally well with a continuous or batch 2-acrylamido-2-methylpropane sulfonic acid production process.

2-Acrylamido-2-methylpropane sulfonic acid may also be prepared according to alternative processes, such as for example the one described in document CN 102952052, which claims the use of acetic anhydride as co-solvent for the acrylonitrile to reduce and control the water content in the reaction to eliminate the use of fuming sulfuric acid.

Isobutylene can be made with various methods known to the person skilled in the art. As examples and without limitation, isobutylene can be obtained by dehydration of tert-butanol or isobutanol, by dehydrogenation of isobutane, by isomerization of but-1-ene or but-2-ene, or by cracking methyl-tert-butyl ether (MTBE), etc.

These production methods have the deficiency of producing by-products such as butene and butadiene. Isolation of isobutylene requires extra steps that increase its production cost.

Butene is understood to mean all unwanted forms that may be present in the isobutylene after its formation. So butene comprises but-1-ene; (Z)-but-2-ene, (E)-but-2-ene, where the latter two forms are isomers.

As already indicated, isobutylene can be purified to reduce the butene and butadiene content. The person skilled in the art knows different purification methods that exist. As an example and in a non-limiting manner, we can cite document US 2014/0051819, which describes purification by absorption of the impure isobutylene mixture by molecular sieves.

Other isobutylene purification methods are also described in documents U.S. Pat. No. 3,479,416 and U.S. Pat. No. 6,242,661.

It has been discovered in a surprising manner by the Applicant that high purity 2-acrylamido-2-methylpropane sulfonic acid can be obtained by controlling the butene and butadiene contents in the isobutylene used as reagent.

Also, the 2-acrylamido-2-methylpropane sulfonic acid purity resulting from the process of the invention is advantageously greater than 99%, more advantageously greater than 99.5%.

According to the invention, the isobutylene comprises less than 1000 ppm of butene, preferably less than 500 ppm, more preferably less than 100 ppm, even more preferably less than 10 ppm.

According to the invention, the isobutylene comprises less than 1000 ppm of butadiene, preferably less than 500 ppm, more preferably less than 100 ppm, even more preferably less than 10 ppm. The ppm are by weight. Here, they are expressed relative to the mass of isobutylene.

The quantity of butene and butadiene is advantageously measured by gas chromatography.

The process that is the subject of the invention may also comprise a step of formation of a 2-acrylamido-2-methylpropane sulfonic acid salt once it has been formed. This is generally a step of neutralization of the —SO₃H acid function in 2-acrylamido-2-methylpropane sulfonic acid. This step may consist of neutralizing all or part of the acid functions. In particular, it allows the formation of an alkali metal salt, an alkaline earth metal salt or an ammonium salt, for example.

The purity of the 2-acrylamido-2-methylpropane sulfonic acid salt resulting from the process of the invention is advantageously greater than 99%, more advantageously greater than 99.5%.

The present invention also relates to obtaining a polymer comprising at least, as monomer, 2-acrylamido-2-methylpropane sulfonic acid, or of its salts, wherein 2-acrylamido-2-methylpropane sulfonic acid is obtained according to the process described previously.

This preparation process for a polymer comprises the following steps:
  preparation of 2-acrylamido-2-methylpropane sulfonic acid by co-reacting acrylonitrile, fuming sulfuric acid and isobutylene, where the isobutylene contains less than 1000 ppm of butadiene and less than 1000 ppm of butene;

polymerization of 2-acrylamido-2-methylpropane sulfonic acid, and/or its neutralized form, alone or in combination with other monomers.

According to a specific embodiment, the 2-acrylamido-2-methylpropane sulfonic acid, and/or its neutralized form, can be polymerized in combination with at least one nonionic monomer.

According to another specific embodiment, the 2-acrylamido-2-methylpropane sulfonic acid, and/or its neutralized form, can be polymerized in combination with at least one cationic monomer.

According to another specific embodiment, the 2-acrylamido-2-methylpropane sulfonic acid, and/or its neutralized form, can be polymerized in combination with at least one anionic monomer.

Accordingly, this process may allow the production of a 2-acrylamido-2-methylpropane sulfonic acid polymer, and/or its neutralized form, and of at least: one nonionic monomer and/or one cationic monomer and/or one anionic monomer.

Accordingly, optionally, the polymer according to the invention may comprise at least one nonionic monomer that is advantageously selected from the group comprising acrylamide, methacrylamide, hydroxyalkyl esters of acrylic acid, hydroxyalkyl esters of methacrylic acid, N-vinyl pyrrolidone, N-vinyl formamide and polyethylene glycol methacrylate. Advantageously, the nonionic monomer is acrylamide.

Optionally, the polymer according to the invention may comprise at least one anionic monomer that is advantageously selected from the group comprising acrylic acid, methacrylic acid, allyl sulfonic acid, or salts thereof. Preferentially, the anionic monomer is acrylic acid or a salt thereof.

Optionally, the polymer according to the invention may comprise at least one cationic monomer that is advantageously selected from the group comprising quaternized or salified dimethyl aminoethyl acrylate, quaternized or salified dimethyl aminoethyl methacrylate, diallyldimethylamine chloride (DADMAC), acrylamidopropyl trimethylamine chloride (APTAC) and methacrylamidopropyl trimethylamine chloride (MAPTAC).

The polymers obtained by the process may be used as dispersants, coagulants, flocculants or thickeners. They are water-soluble or water-absorbing.

The polymers obtained by the process may be linear, branched, crosslinked, or comb.

The invention also relates to the polymers previously described, as well as their use in the fields of enhanced oil and gas recovery (drilling, hydraulic fracturing, EOR, drag reduction), water treatment, agriculture, paper, mines, cosmetics, detergents, textiles, and construction.

EXAMPLES

Protocol for Preparation of 2-Acrylamido-2-Methylpropane Sulfonic Acid

To a stirred, 2000-mL, jacketed reactor, 1525 grams of acrylonitrile was added and 117.2 grams of fuming sulfuric acid titrating at 103% $H_2SO_4$ (13% Oleum). The mixture was stirred and cooled via the reactor jacket, which was held at −20° C.

To the previous mixture, 97 grams of isobutylene was added, at a flow rate of 1.6 grams/minute.

The temperature of the mixture was controlled at 45° C. while isobutylene was added. The crystals of 2-acrylamido-2-methylpropane sulfonic acid precipitated in the mixture and the solid content was about 20% by weight. The mixture was filtered on a Buchner-type filter, and the white crystals were washed twice with 300 grams of virgin acrylonitrile.

The resulting solids were dried under vacuum at 50° C. for two hours.

The purity of the 2-acrylamido-2-methylpropane sulfonic acid was measured by HPLC (high-performance liquid chromatography) using the following conditions:

ODS-3 column (GL Science trademark);
Mobile phase: water with 0.03% trifluoroacetic acid/Acetonitrile (mass ratio 90/10);
Mobile phase flow rate: 0.8 $cm^3$/minute (0.8 mL/minute);
Detection wavelength: 200 nm;

The quantities of butene and butadiene were measured by gas chromatography using the following conditions:

Petrocol DH column, 100 m×0.25 mm ID, 0.5 μm film;
Oven: from −50° C. (10 min) to 75° C. with a gradient of 5° C./min;
Detector: FID;
Injection volume: 250 μL;
Carrier gas: Helium;
Division ratio: 100:1.

Different isobutylene and 2-acrylamido-2-methylpropane sulfonic acid purities were tested using the protocol above.

TABLE 1

Purity of isobutylene and 2-acrylamido-2-methylpropane sulfonic acid obtained from isobutylene

| | Isobutylene purity | | 2-Acrylamido-2- |
| --- | --- | --- | --- |
| | Butene quantity (ppm) | Butadiene quantity (ppm) | methylpropane sulfonic acid purity (mass %) |
| Example 1 (invention) | 1 | 1 | 99.8 |
| Example 2 (invention) | 20 | 10 | 99.7 |
| Example 3 (invention) | 8 | 3 | 99.8 |
| Example 4 (invention) | 4 | 2 | 99.8 |
| Example 5 | 200 | 120 | 99.4 |
| Example 6 | 800 | 520 | 99.1% |
| Example 7 (counter-example) | 1250 | 1100 | 98.5% |

According to the results, it appears clearly that the 2-acrylamido-2-methylpropane sulfonic acid has better purity if the impurities contained in the isobutylene are controlled at a level less than 1000 ppm.

The purity difference between examples 1 to 6 and example 7 is significant in this domain of 2-acrylamido-2-methylpropane sulfonic acid production.

Protocol for Polymerization of a 2-Acrylamido-2-Methylpropane Sulfonic Acid and Acrylamide Copolymer To 60 grams of water was added 40 grams of 2-acrylamido-2-methylpropane sulfonic acid obtained according to examples 1 to 5. A caustic solution of 50% by weight NaOH was added so as to make the pH 8. Water was then added to adjust the concentration of the 2-acrylamido-2-methylpropane sulfonic acid sodium salt to 35% by weight.

55.6 grams of an aqueous solution of acrylamide at 40% by weight was added, and extra water was added again to adjust the total quantity of monomer to 35% by weight.

700 mg of an azo initiator was added in one portion to the previous mixture.

730 mg of sodium persulfate and 700 mg of sodium sulfite were added to initiate polymerization. The reaction was finished after 3 hours. The gel obtained was then cut, dried and sieved.

Test Protocol for UL Viscosity.

500 mg of polymer was added to 490 mL of a deionized water solution. After complete dissolution of the polymer, 29.25 grams of NaCl was added.

The viscosity was measured using a Brookfield digital DVII+ viscosimeter on a rotation rate of 60 rpm at 25° C. (UL module).

Test Protocol for Insolubles Content in Water.

1 g of polymer was dissolved in 200 mL of a deionized water solution. A wire mesh with pore size 200 μm was dried and weighed to measure mass m1.

The polymer solution was then filtered on the wire mesh. The wire mesh was then dried in the oven at 105° C. for 4 hours, and then weighed to measure mass m2.

The insolubles content was calculated using the formula:

% Insolubles=100*(M2−M1)

The results for all of the polymers are given in Table 2. The performance of the polymers was evaluated by measuring the viscosity directly connected to the molecular weight, both of which should be as high as possible. It was also evaluated by measuring the lowest possible target solubles content.

TABLE 2

UL viscosity and insolubles content of the polymers obtained from different 2-acrylamido-2-methylpropane sulfonic acids

| | Origin of 2-acrylamido-2-methylpropane sulfonic acid | UL viscosity (mPa · s (cps)) | Insolubles content in water (%) |
|---|---|---|---|
| Polymer 1 | Example 1 (invention) | 5.2 (5.2) | 0 |
| Polymer 2 | Example 2 (invention) | 4.8 (4.8) | 0.01 |
| Polymer 3 | Example 3 (invention) | 5.0 (5.0) | 0.008 |
| Polymer 4 | Example 4 (invention) | 5.1 (5.1) | 0 |
| Polymer 5 | Example 5 (invention) | 4.6 (4.6) | 0.1 |
| Polymer 6 | Example 6 (invention) | 4.4 (4.4) | 1 |
| Polymer 7 | Example 7 (counter-example) | 4 (4) | 3 |

The polymers obtained from 2-acrylamido-2-methylpropane sulfonic acid according to the invention have improved performances, both in terms of UL viscosity and of insolubles content.

Examples 8 and 9 that follow are to demonstrate that producing ATBS according to the invention produces polymers that do not require a complex and burdensome purification step.

Example 8: Purification of 2-Acrylamido-2-Methylpropane Sulfonic Acid Obtained According to Example 7 According to U.S. Pat. No. 4,337,215.

To a jacketed, 2000 mL, stirred reactor, 1350 grams of glacial acetic acid and 150 grams of water were added.

500 grams of the monomer obtained in example 7 was added to the reactor. The resulting suspension was stirred.

The mixture was heated to 90° C. to completely dissolve the 2-acrylamido-2-methylpropane sulfonic acid.

After dissolution, the mixture was cooled at a rate of 2° C./5 minutes, to a final temperature of 15° C. The suspension of crystals was held at 15° C. for 1 hour, and then filtered over a Buchner filter. The crystals obtained were washed twice with 300 grams of glacial acetic acid.

The crystals were dried under vacuum at a temperature of 60° C. for 3 hours.

The dry crystals weighed 343 grams, i.e. a 68% yield. The purity was 99.3%, i.e. purity that corresponds to that obtained according to the process of the invention, in particular in examples 5 and 6 for which no 2-acrylamido-2-methylpropane sulfonic acid purification step is made.

Example 9

The purified monomer obtained in example 8 was copolymerized according to the protocol described previously. The UL viscosity results and the insolubles content are given in Table 3 below.

TABLE 3

UL viscosity and insolubles content of the polymer obtained from 2-acrylamido-2-methylpropane sulfonic acid from example 8.

| | Origin of 2-acrylamido-2-methylpropane sulfonic acid | UL viscosity (mPa · s (cps)) | Insolubles content in water (%) |
|---|---|---|---|
| Polymer 8 | Example 8 | 4.5 (4.5) | 0.12 |

Polymer 8 has similar properties to polymer 5, but the 2-acrylamido-2-methylpropane sulfonic acid used to produce it had to undergo a purification step, which was not the case for polymer 5.

The invention claimed is:

1. A production process for 2-acrylamido-2-methylpropane sulfonic acid, the process comprising co-reacting acrylonitrile, fuming sulfuric acid and isobutylene, wherein the isobutylene contains less than 1000 ppm of butadiene and less than 1000 ppm of butene, and wherein the 2-acrylamido-2-methylpropane sulfonic acid presents purity greater than 99.5%.

2. The process according to claim 1, wherein the isobutylene contains less than 10 ppm of butadiene.

3. The process according to claim 1, wherein the isobutylene contains less than 10 ppm of butene.

4. The process according to claim 1, comprising, after forming the 2-acrylamido-2-methylpropane sulfonic acid, further processing to form a salt of 2-acrylamido-2-methylpropane sulfonic acid.

5. The process according to claim 1, wherein the isobutylene contains less than 10 ppm of butadiene and less than 10 ppm of butene.

6. A process for preparing a polymer, said process comprising the following steps:
    preparing of 2-acrylamido-2-methylpropane sulfonic acid according to claim 1; and
    polymerizing of 2 acrylamido-2-methylpropane sulfonic acid and/or a neutralized form thereof, alone or in combination with other monomers.

7. The process according to claim 6, wherein the 2-acrylamido-2-methylpropane sulfonic acid, and/or its neutralized form, is polymerized in combination with at least one nonionic monomer.

8. The process according to claim 6, wherein the 2-acrylamido-2-methylpropane sulfonic acid, and/or its neutralized form, is polymerized in combination with at least one cationic monomer.

9. The process according to claim 6, wherein the 2-acrylamido-2-methylpropane sulfonic acid, and/or its neutralized form, is polymerized in combination with at least one anionic monomer.

10. The process according to claim 7, wherein the 2-acrylamido-2-methylpropane sulfonic acid, and/or its neutralized form, is polymerized in combination with at least one cationic monomer.

11. A process according to claim 10, wherein the isobutylene contains less than 10 ppm of butadiene and less than 10 ppm of butene.

12. The process according to claim 7, wherein the 2-acrylamido-2-methylpropane sulfonic acid, and/or its neutralized form, is polymerized in combination with at least one anionic monomer.

13. The process according to claim 12, wherein the isobutylene contains less than 10 ppm of butadiene and less than 10 ppm of butene.

14. The process according to claim 2, comprising, after forming the 2-acrylamido-2-methylpropane sulfonic acid, further processing to form a salt of 2-acrylamido-2-methylpropane sulfonic acid.

15. The process according to claim 3, comprising, after forming the 2-acrylamido-2-methylpropane sulfonic acid, further processing to form a salt of 2-acrylamido-2-methylpropane sulfonic acid.

16. A process for preparing a polymer, said process comprising the following steps:

preparing 2-acrylamido-2-methylpropane sulfonic acid according to claim 2; and polymerizing 2-acrylamido-2-methylpropane sulfonic acid and/or a neutralized form thereof, alone or in combination with other monomers.

17. A process for preparing a polymer, said process comprising the following steps:

preparing 2-acrylamido-2-methylpropane sulfonic acid according to claim 3; and polymerizing 2-acrylamido-2-methylpropane sulfonic acid and/or a neutralized form thereof, alone or in combination with other monomers.

* * * * *

UNITED STATES PATENT AND TRADEMARK OFFICE
CERTIFICATE OF CORRECTION

PATENT NO. : 10,662,149 B2
APPLICATION NO. : 15/753577
DATED : May 26, 2020
INVENTOR(S) : Favero et al.

It is certified that error appears in the above-identified patent and that said Letters Patent is hereby corrected as shown below:

In the Claims

Column 8, Lines 38 and 39: Claim 1, Delete "less than 1000 ppm of butadiene and less than 1000 ppm of butene," and insert -- less than 100 ppm of butadiene and less than 100 ppm of butene, --

Signed and Sealed this
Eighteenth Day of August, 2020

Andrei Iancu
*Director of the United States Patent and Trademark Office*